United States Patent [19]
Hüppi et al.

[11] 4,139,367
[45] Feb. 13, 1979

[54] PIPERIDINE SALTS AS PLANT GROWTH REGULANTS

[75] Inventors: Gerhard Hüppi, Gockhausen; Wijitha DeSilva, Schöfflisdorf; Gottlieb Ryser, Basel, all of Switzerland

[73] Assignee: Hoffmann-La Roche Inc., Nutley, N.J.

[21] Appl. No.: 737,968

[22] Filed: Nov. 2, 1976

Related U.S. Application Data

[62] Division of Ser. No. 531,134, Dec. 9, 1974, Pat. No. 4,014,678.

[30] Foreign Application Priority Data

Dec. 14, 1973 [CH] Switzerland ............... 17546/73

[51] Int. Cl.² .......................... A01N 5/00; A01N 9/22; C07D 211/06
[52] U.S. Cl. ........................................... 71/94; 71/76; 71/74
[58] Field of Search .................. 71/94, 76; 260/293.51

[56] References Cited
U.S. PATENT DOCUMENTS 3,850,611  11/1974  Naranishi et al. ................. 71/94 X

FOREIGN PATENT DOCUMENTS 2172418  9/1973  France ......................... 71/94

*Primary Examiner*—Catherine L. Mills
*Attorney, Agent, or Firm*—Jon S. Saxe; Bernard S. Leon; William M. Farley

[57] ABSTRACT

Compounds represented by the formula

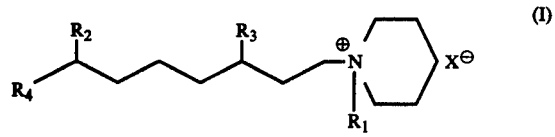

wherein $R_1$ is lower alkyl having 1–4 carbons, lower alkenyl having 2–4 carbons or lower alkynyl having 2–4 carbons; $R_2$, $R_3$ and $R_4$ each are a lower alkyl having 1–4 carbons or $R_2$ and $R_4$ together with the carbon to which they are attached are a 5 or 6 membered alicyclic ring; and X is chlorine, bromine or iodine;

their use as plant growth regulants and plant growth regulant compositions containing the active compounds are disclosed.

8 Claims, No Drawings

PIPERIDINE SALTS AS PLANT GROWTH REGULANTS

This is a division of application Ser. No. 531,134 filed Dec. 9, 1974, now U.S. Pat. No. 4,014,678.

DESCRIPTION OF THE INVENTION

This invention relates to quaternized piperidine salts displaying plant growth regulant activity, processes for their preparation, compositions containing them as the active ingredient and methods for the regulation of plant growth using one or more of said salts.

The active quaternized piperidine salts provided by the present invention are represented by the formula

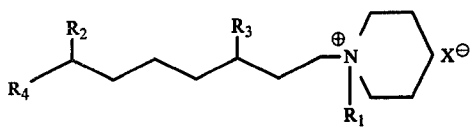

wherein $R_1$ is lower alkyl having 1–4 carbon atoms, lower alkenyl having 2–4 carbon atoms or lower alkynyl having 2–4 carbon atoms; $R_2$, $R_3$ and $R_4$ each are a lower alkyl containing 1–4 carbon atoms or $R_2$ and $R_4$ together with carbon atom to which they are attached form a 5- or 6-membered alicyclic ring; and X is chlorine, bromine or iodine.

As used in Formula I and throughout the specification, alkyl, alkenyl and alkynyl include straight chain or branched chain groups, e.g., methyl, ethyl, propyl, isopropyl, butyl, vinyl, propenyl, propargyl and the like.

Preferred compounds of this invention within the scope of Formula I are 1-(3,7-dimethyloctyl)-1-methylpiperidinium iodide, 1-(3,7-dimethyloctyl)-1-(2-propenyl)piperidinium bromide and 1-(3,7-dimethyloctyl)-1-(2-propynyl)-piperidinium bromide.

The expression "plant growth regulator" as used herein denotes compounds which either retard or stimulate the growth of main or side branches or shoots of plants. It includes compounds which are capable of influencing the flower formation, the onset of flowers, the shoot or branch formation, the parthenocarpy, the falling of fruit and/or leaves and the ripening of fruit and/or leaves with or without the prior application of fertilizers. Plant growth regulator compounds also have an effect on the transport of substances within the plants, for example, a stimulation of the latex flow and/or the metabolism or, for example, an increase in the sugar content within the plant.

In shrubs, for example, this plant growth regulating activity produces a retardation of the growth in height with concomitant stimulation of the side-growth.

The compounds of Formula I are particularly useful as plant growth regulators. The compounds have both pre-emergence and post-emergence plant growth regulating activity, but they are especially useful when they are used as post-emergence plant growth regulators.

The compounds of Formula I are especially active in and against the following plants, especially young plants:

(a) Cereals and grains such as corn, rice, wheat, rye, barley, oats;

(b) Woody fruit or nut bearing trees and shrubs such as apple, pear, peach, cherry, lemon, cocoa, tea, coffee, banana, gum, olive and walnut;

(c) Plants used in landscaping such as privet, hornbeam, white cedar, juniper, rose, azalea, chrysanthemum, poinsettia, cyclamen, pyracantha, forsythia, magnolia, petunia and bromeliad;

(d) Non-woody plants grown for commercial purposes such as cotton, soya bean, groundnut, tobacco, flax, sugar beet and pineapple;

(e) Vegetables such as Solanaceae, tomatoes, legumes, pumpkins, melons;

(f) Berries such as strawberries, bilberries, raspberries, blueberries, blackberries and redcurrants.

The compounds of Formula I are also useful for reducing the pruning of vines in a vineyard and reducing or eliminating the harmful effects of general pollution on plants, e.g., the effect of ozone or sulfur dioxide.

The active compounds of this invention have activity as pre-emergent and post-emergent plant growth regulants. However, the predominant activity is manifested post-emergent. The active compounds can be applied to the plants or soil in conventional carries usually used for such applications to plants. Thus, the compounds can be applied as a liquid spray, dust, granulate or wettable powder. They can be formed into solutions, emulsions, emulsifiable concentrates, dispersions, dusts, granulates or wettable powders when mixed with agriculturally acceptable adjuvants, modifiers, diluents or conditioning agents commonly used with plant growth regulating agents. The effective amount of active compound in the plant regulating compositions of this invention, in association with one or more of the agriculturally acceptable compatible carriers described herein is generally from about 0.01% to 95% by weight of one or more active compound. When a concentrate is used, about 40% to 95% of active compound or mixture thereof is suitable.

Liquid formulations suitable for directly spraying plant growth regulants onto the plants can be prepared as aqueous solutions or as organic solutions. A typical suitable organic solvent useful for forming plant growth regulant sprayable compositions is a mixed solvent containing acetone, methanol and dimethylformamide. A suitable ratio of the components in the solvent mixture on a volume basis is 90 volumes acetone, 8 volumes methanol and 2 volumes dimethylformamide. The amount of active compounds of this invention in the sprayable compositions varies according to the compounds used, plants treated, effects desired, weather conditions and whether the application is to the plant directly or the soil. Generally, treatment through the soil requires a higher concentration than direct application to the plant. The sprayable liquid compositions thus contain an amount of the active compound or mixtures thereof which is effective for the plant growth regulation effect desired. It has been found that from about 0.01% to about 50% by weight is suitable with about 0.01% to 25% preferred.

Emulsifiable concentrates containing an active compound of Formula I or mixtures thereof, depending on the solubility of the compound, can be prepared using suitable agriculturally acceptable solvents such as N-methylpyrrolidine, dimethylformamide and the like. Surface-active agents, e.g., wetting agents, dispersants, emulsifiers should be added in a sufficient amount to produce a formulation having the desired characteristics. The amount of active compound in the concentrate varies, depending on the effect desired, mode and site of treatment, plants treated, weather conditions and compounds or mixtures thereof used. Generally, the emulsifiable concentrates contain an amount of active compound sufficient to achieve the desired plant growth regulant effect. Generally, about 25% to 50% by weight of active compound is used.

Various application forms can be better adapted to the various purposes for which the active compounds may be used if substances which improve the dispersion, adhesion, penetration and resistance to rain are added. Such substances include fatty acids, waxes, resins, wetting agents, emulsifiers, mineral oils, vegetable oils, binding agents and the like. In a similar manner, the biological spectrum of the active plant growth regulating compounds may be greatly broadened by the addition to the plant growth regulating compositions of substances having bactericidal, herbicidal or fungicidal properties or by the addition of fertilizers, chelate-forming agents and other plant growth regulators.

Examples of herbicides and plant growth regulators which can be present in the compositions provided by the present invention are:

2,2-dichloropropionic acid,
N-(4-aminobenzenesulfonyl)methylcarbamate,
4-chloro-4-ethylamino-6-isopropylamino-1,3,5-triazine,
4-chloro-2-oxobenzothiazolin-3-yl-acetic acid,
5-bromo-6-methyl-3-(1-methyl-n-propyl)uracil,
3,5-dibromo-4-hydroxybenzonitrile,
D,N-ethyl-2-(phenylcarbanoyloxy)propionamide,
N-(4-bromo-3-chlorophenyl)-N'-methoxy-N'-methylurea,
methyl 2-chloro-9-hydroxyfluorene-9-carboxylate,
N'-4-(4-chlorophenoxy)-phenyl-N,N-dimethylurea,
isopropyl-N-(3-chlorophenyl)carbamate,
2,3,5,6-tetrachloroterephthalic acid dimethyl ester (DCPA),
2,4-dichlorophenoxyacetic acid,
4-isopropylamino-6-methylamino-2-methylthio-1,3,5-triazine,
n-butyl 9-hydroxyfluorene-9-carboxylate,
ethylene,
naphthoxyacetic acid,
3,6-dichloro-2-methoxybenzoic acid,
(+)-2-(2,4-dichlorophenoxy)propionic acid,
9,10-dihydro-8a,10a-diazoniaphenanthrene-2A,
N'-(3,4-dichlorophenyl)-N,N-dimethylurea,
gibberellic acid,
indolylacetic acid,
indolylbutyric acid,
4-hydroxy-3,5-diiodobenzonitrile,
N'-(3,4-dichlorophenyl)-N-methoxy-N-methylurea,
(4-chloro-2-methylphenoxy)acetic acid,
4-(4-chloro-2-methylphenoxy)butyric acid,
(+)-2-(4-chloro-2-methylphenoxy)propionic acid,
N-(benzothiazol-2-yl)-N,N'-dimethylurea,
N'-(3-chloro-4-methoxyphenyl)-N,N-dimethylurea,
1,2,3,6-tetrahydro-3,6-dioxopyridazine,
N'-(4-chlorophenyl)-N-methoxy-N-methylurea,
N'-(4-chlorophenyl)-N,N-dimethylurea,
naphthylacetic acid,
N-1-naphthylphthalamic acid,
2,4-dichlorophenyl 4-nitrophenyl ether,
1,1'-dimethyl-4,4'-bipyridylium-2A,
3-(m-tolylcarbamoyloxy)phenyl carbamate,
4-amino-3,5,6-trichloropicolinic acid,
4,6-bis-isopropylamino-2-methylthio-1,3,5-triazine,
N-(3,4-dichlorophenyl)-propionamide,
isopropyl-N-phenylcarbamate,
5-amino-4-chloro-2-phenylpyridazin-3(2H)-one,
N-dimethylaminosuccinic acid,
2-chloroethylphosphorus acid,
tributyl-2,4-dichlorobenzoyl-phosphonium chloride,
2,4,5-trichlorophenoxypropionic acid,
2,3,6-trichlorobenzoic acid,
2-chloro-4,6-bis-ethylamino-1,3,5-triazine,
sodium chloroacetate,
2,4,5-trichlorophenoxyacetic acid,
5-chloro-6-methyl-3-tert.butyluracil,
4-ethylamino-2-methylthio-6-tert.butylamino-1,3,5-triazine-(tert.butyryn),
2,3,5-triiodobenzoic acid and
1,1,4-trimethyl-6-isopropyl-5-priopionyl-indane.

Examples of fungicides which may be present in the plant growth regulating compositions provided by the present invention are:

2,4-dichloro-6-(o-chloraniline)-S-triazine,
2,4,5,6-tetrachloroisophthalic acid nitrile,
p-dimethylaminophenyldiazo sodium sulfonate,
1,4-dichloro-2,5-dimethoxybenzene,
manganese ethylene-bis-dithiocarbamate,
zinc ethylene-bis-dithiocarbamate,
coordination product from zinc and manganese ethylene-bisdithiocarbamate,
methyl 1-(butylcarbamoyl)-2-benzimidazole carbamate,
2-(4-thiazole)-benzimidazole and
cis-N-[(trichloromethyl)-thio]-4-cyclohexene-1,2-dicarboximide.

The amount of the compounds of Formula I which is applied varies depending on the conditions of use, effect desired, plants treated and active compounds used. However, experience has shown that the results set forth hereinafter are realistic bases for determining application rates in general. For example, the amount can vary not only between different species of plants but also within a specific species, depending on factors such as the size and the age of the plants, the particular active compound used, the time of year, the type of soil and climatic conditions at the time of use such as the air temperature, light intensity, rain and wind. Furthermore, if the active compounds or the plant growth regulating compositions come into contact with the plant via irrigation of the soil, higher concentrations will be necessary since, with this type of use, the plant is indirectly treated in comparison with a direct treatment by application of the active compound or plant growth regulating composition on leaves and stems, e.g., by spraying.

Accordingly, the amount of active compound present in the plant growth regulating compositions varies according to the plants to be controlled, the amount required for application, the method of application, the particular compound used and the degree of regulation of plant growth which is desired. In general, the compositions of this invention contain less than 50% by weight of active compound in a ready-for-use spray form. They can contain as little as 0.01% by weight and still be effective.

In principle, the amount of active compound which is used is chosen so that an effective control of the plant growth is achieved. Accordingly, the choice of the minimum amount of active compound used is governed by the minimum amount of compound which is able to effect the lower limit of growth retardation desired. The choice of the maximum amount of active compound used is correspondingly governed by that amount of compound which is able to bring about the upper limit of growth retardation desired. In the case of tomato plants, the criteria for an effective growth retardation are of such a nature that a dwarfed plant which has no loss in fruit quality or quantity is particularly desired. The parameters for an effective growth regulating activity in such plants are retarded growth in height and increased or non-retarded side-growth as a minimum effect and retarded growth in height and retarded side-growth as a maximum effect. The amount of active compound which causes these criteria to be met is determined by the characteristics, for example, of the tomato plant.

In order to achieve the greatest post-emergence growth regulating activity, amounts of 0.5 kg. to 10 kg. or more per hectare of active compound are used. In a similar manner, the greatest post-emergence growth regulating activity is generally obtained using amounts of active compound which lie between 1 kg. and 5 kg. per hectare. A preferred range for spray solutions lies between 10 parts per million and 100,000 parts per million on a weight basis of active compound depending on the plant species to be treated and the particular compound chosen. An especially preferred amount generally lies between 100 parts per million and 10,000 parts per million.

The active compounds of this invention are advantageous because they do not have a lasting effect on the plants or a regulating activity which remains in the soil. The compounds of Formula I decompose slowly and there is accordingly a consequent slow reduction in activity. This effect has advantages since (a) a short-term effect which may be lengthened by subsequent further treatment is produced;

(b) the normal growth behavior of the plant re-occurs in step with the decrease in activity; and (c) no harmful residues remain either on the plant or in the soil.

The duration of the retardation effect varies according to the particular compound used and other factors such as the type of plant treated, climatic conditions etc.

Although the compounds of Formula I possess a plant growth regulating activity, they are vitually non-toxic to animals.

It will, of course, be appreciated that not all of the compounds of Formula I are active against all plants. Each of the compounds does, however, possess activity against a specific plant or plants and this activity is a function of the particular compound. As will be evident from the following, a particular advantage of the present invention is that the plant growth regulating compositions possess pre-emergence and post-emergence plant growth regulating activity when used for the treatment of various plants, the range of plants being extremely wide. The growth regulating activity of the compounds of this invention will be evident from the following micro-test for the determination of the post-emergence activity.

Several concentrations of active compound are sprayed on to the plant so that a complete spray coating is obtained or the roots are watered with just sufficient active compound solution for the pot in which the plant is standing to hold without liquid being drained into the supporting dish for the pot, the amount required is previously determined in a blind test using water.

The compound is dissolved in water and the solution treated with 0.1% Tween 20 [polyoxyethylene (20) sorbitan monolaurate, Atlas Chemical Industries, Inc., Wilmington, Del.].

In a treatment of the roots of Petunia hybrida of the "Furore" type, the height of the plant in comparison to an untreated control was measured after 5 weeks. The results are given in Table I as a percentage reduction relative to the control. N-Dimethylamino-succinic acid hemihydrazide (Alar) was used as the standard.

Table I

| Compound | Concentration ppm | Root Treatment Type of Application | % Reduction |
|---|---|---|---|
| 1-(3,7-dimethyloctyl)-1-(2-propenyl)-piperidinium bromide | 1500 | 20 ml. per pot | 35 |
| Alar | 2000 | 20 ml. per pot | 31 |

In a treatment of the supraterranean plant parts of *Chrysanthemum morfolium* using a complete spray coating, the side sprouting was measured after 60 days. The results are given in Table II as a percentage reduction of growth of the side sprouting in comparison to an untreated control. N-dimethylamino-succinic acid hemihydrazide (Alar) was used as the standard.

Table II

| Compound | Concentration ppm | % Reduction |
|---|---|---|
| 1-(3,7-dimethyloctyl)-1-(2-propenyl)-piperidinium bromide | 4000 | 51 |
| Alar | 4000 | 7 |

The compounds within the scope of Formula I are prepared by either (a) reacting a compound represented by the formula

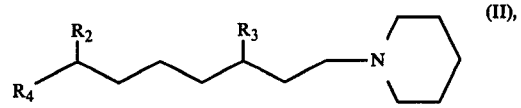

wherein $R_2$, $R_3$ and $R_4$ have the significance given in Formula I,
with a compound represented by the formula

$$R_1X \quad \text{(III),}$$

wherein $R_1$ and X have the significance given in Formula I, or (b) reacting a compound represented by the formula

wherein $R_1$ has the significance given in Formula I, with a compound represented by the formula

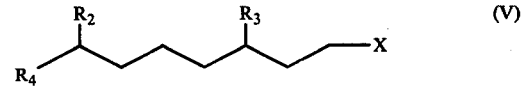

wherein $R_2$, $R_3$, $R_4$ and X have the significance given in Formula I.

According to embodiment (a), a compound within the scope of Formula II is reacted with an appropriate lower alkylating, lower alkenylating or lower alkynylating agent. For this purpose, a compound of Formula II is dissolved in a lower alkanol, e.g., preferably methanol or ethanol, an ether, e.g., dioxane, a di(-lower alkyl) ketone, e.g., acetone, dimethylformamide, a chlorinated hydrocarbon, e.g., chloroform, carbon tetrachloride or methylene chloride or a hydrocarbon, e.g., benzene or toluene, preferably in ethanol or benzene. The resulting solution is then reacted with the desired lower alkylating, lower alkenylating or lower alkynylating agent. As such agents there may be used conventional lower alkylating, lower alkenylating or lower alkynylating agents such as, for example, the chlorides, bromides or iodides of the appropriate lower alkyl, lower alkenyl or lower alkynol compound. The reaction is advantageously carried out at a temperature between 0° C. and 60° C., preferably at room temperature. The pressure is not critical since the reaction can be carried out in an open vessel.

In the process provided by the present invention, the preferred starting materials are compounds of Formula II. The compounds of Formual II are expediently prepared by catalytically hydrogenating a compound represented by the formula

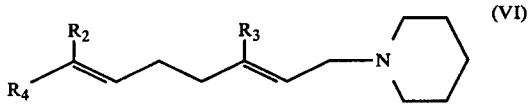

(VI)

wherein $R_2$, $R_3$ and $R_4$ have the significance given in Formula I.

In carrying out this catalytic hydrogenation, a compound of Formula VI is dissolved in a lower alkanol, preferably ethanol, and treated with the catalyst, preferably 5% palladium-carbon or platinum oxide. The reaction mixture is expediently hydrogenated at room temperature with occasional cooling until hydrogen is no longer taken up. The catalyst is filtered off and the filtrate evaporated. The residue is distilled over a Vigreux column in a high vacuum.

The following Example illustrates the preparation of the active compounds.

EXAMPLE 1

Preparation of 1-(3,7-dimethyloctyl)-1-(2-propenyl)-piperidinium (a) 2440 G. of piperidine dissolved in 7 liters of low-boiling petroleum ether are added to a 20 liter reaction flask provided with a stirrer, condenser, dropping funnel and drying tube. The mixture is cooled to 5° C. using an ice/methanol bath. 3927 G. of geranyl bromide are then added dropwise at 5° to 10° C. over a period of 1 hour. The resulting mixture is stirred overnight without replacing the cooling bath and is then transferred to a 50 liter stirring vessel and stirred with 20 liters of 1-N hydrochloric acid. The aqueous phase is extracted twice with 5 liters of low-boiling petroleum ether each time. The organic phases are combined, back-extracted twice with 2 liters of 1-N hydrochloric acid each time and then discarded. The aqueous extracts are combined, made alkaline with ca 2 liters of concentrated sodium hydroxide solution and then extracted three times with 30 liters of low-boiling petroleum ether each time. The extracts are each washed twice with 5 liters of saturated sodium chloride solution, dried over sodium sulfate and evaporated. The residue is distilled over a small Vigreux column in a high vacuum, there being obtained geranyl piperidine in the form of a yellowish oil; boiling point$_{0.8}$ = 95°–100° C.

(b) 6000 G. (27.15 mol) of geranyl piperidine are dissolved in 6 liters of alcohol and introduced into a 20 liter hydrogenation flask. 300 G. of 5% palladium-carbon are added and the mixture is hydrogenated room temperature with occasional cooling until the hydrogen uptake comes to a standstill. The catalyst is filtered off and the filtrate evaporated. The residue is distilled in a high vacuum over a small Vigreux column. There is thus obtained tetrahydrogeranylpiperidine; boiling point$_{0.7}$ = 86°–88° C.

(c) 2883 G. (12.8 mol.) of tetrahydrogeranylpiperidine are introduced into a three-necked flask provided with a reflux condenser, stirrer and gas inlet tube. 2030 G. (16.9 mol.) of allyl bromide in 11.5 liters of absolute alcohol are added under an inert gas atmosphere while stirring. The reaction mixture is stirred at room temperature for 3 days. The mixture is then evaporated in a rotary evaporator and the residual, almost colorless, oil dried for 48 hours in a high vacuum. There is thus obtained 1-(3,7-dimethyloctyl)-1-(2-propenyl)-piperidinium bromide in the form of an almost colorless oil; $n_D^{24}$ = 1.5243.

In an analogous manner, but using propargyl bromide in place of allyl bromide, there is obtained 1-(3,7-dimethyloctyl)-1-(2-propynyl)piperidinium bromide as a yellow oil; $n_D^{24}$ = 1.5165.

In an analogous manner, but using methyl iodide in place of allyl bromide, there is obtained 1-(3,7-dimethyloctyl)-1-methylpiperidinium iodide; melting point 134°–136° C.

We claim:

1. A compound represented by the formula

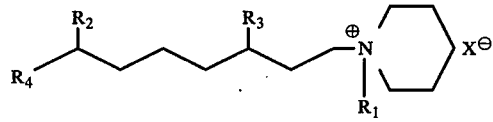

wherein $R_1$ is lower alkyl having 1–4 carbons, $R_2$, $R_3$ and $R_4$ each are lower alkyl having 1–4 carbons and X is chlorine, bromine or iodine.

2. 1-(3,7-Dimethyloctyl)-1-methylpiperidinium iodide.

3. A composition for the regulation of plant growth consisting essentially of an effective amount of one or more of the compounds of claim 1 in association with a compatible agriculturally acceptable carrier.

4. A composition according to claim 3, wherein said compound is 1-(3,7-dimethyloctyl)-1-methylpiperidinium iodide.

5. A composition according to claim 3 which contains from 0.01% to 95% by weight of at least one compound of claim 1.

6. A composition according to claim 5 in the form of a concentrate which contains from about 40% to 95% of at least one compound of claim 1.

7. A composition according to claim 5 in a form suitable for spraying which contains from about 0.1% to 25% of at least one compound of claim 1.

8. A method for the regulation of plant growth which comprises treating the plants to be regulated with an amount of a composition containing an effective amount of one or more of the compounds represented by the formula
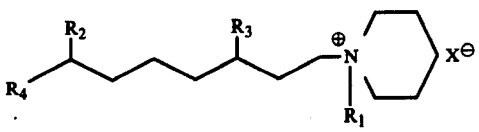
wherein $R_1$ is lower alkyl having 1–4 carbons; $R_2$, $R_3$ and $R_4$ each are lower alkyl having 1–4 carbons and X is chlorine, bromine or iodine, in association with a compatible agriculturally acceptable carrier.
* * * * *